United States Patent [19]
Drauz et al.

[11] Patent Number: 6,156,908
[45] Date of Patent: Dec. 5, 2000

[54] PROCEDURE FOR THE MANUFACTURE OF 3-AMINO-2-OXO-PYRROLIDINES, NEW INTERMEDIATES AND THEIR USE

[75] Inventors: Karlheinz Drauz, Freigericht; Ingo Klement, Pohlheim; Gunter Knaup, Bruchkobel, all of Germany

[73] Assignee: Rohm Gesellschaft, GmbH, Dartmstadt, Germany

[21] Appl. No.: 09/393,874

[22] Filed: Sep. 10, 1999

[30] Foreign Application Priority Data

Sep. 11, 1998 [DE] Germany ............................ 198 41 895

[51] Int. Cl.[7] ...................... C07D 207/40; C07D 315/00; C07D 321/00
[52] U.S. Cl. .......................... 548/546; 562/556; 562/559
[58] Field of Search .............. 548/546; 562/559, 562/556

[56] References Cited

U.S. PATENT DOCUMENTS 5,484,946 1/1996 Abood et al. .

FOREIGN PATENT DOCUMENTS

94/22820 10/1994 WIPO .

OTHER PUBLICATIONS

German Patent Office communication dated Sep. 15, 1998.

"Protected Lactam–Bridged Dipeptides for Use as Conformational Constraints in Peptides", 1982 Amer. Chem. Soc., pp. 104–198, vol. 47, No. 1.

"Decrease of a–Helix Potential and Biological Activity of b–Endorphin in Response to Modifications of MET[5]", Neuropeptides : 47–51, 1980.

Methiomine Studies VII, May, 1945, pp. 849–851,Toennies, et al, 1945.

"Preparation of D–,DL, and L–Homoserine Lactone from Methionine", Microchem. Journal, 40, 226–232 (1989).

"The Reaction of Idoacetate with Methionine", Journal of Biol. Chem. vol. 234, No. 7, Jul. 1959, pp. 1761–1765.

*Primary Examiner*—Deborah C. Lambkin
*Attorney, Agent, or Firm*—Omri M. Behr, Esq.

[57] ABSTRACT

The invention is directed to a process for the preparation of lactams of Formula I. It is further directed to new advantageous intermediates of Formula II and the use thereof. By the cyclization of compounds of Formula II, compounds of Formula I are obtained.

25 Claims, No Drawings

PROCEDURE FOR THE MANUFACTURE OF 3-AMINO-2-OXO-PYRROLIDINES, NEW INTERMEDIATES AND THEIR USE

FIELD OF THE INVENTION

3-Amino-2-Oxo-Pyrrolidines, intermediates therefor and use thereof.

DISCUSSION OF THE PRIOR ART

3-Amino-2-oxo-pyrrolidine is preferred as a building block for peptide mimics which may be utilized as pharmaceuticals. In WO 94/22820, for example, 3-amino-1-phenyl-2-oxo-pyrroldines substituted in the phenyl ring are utilized as intermediate products for thrombocyte aggregation inhibitors. Further, these gamma lactam containing bioactive combinations were investigated by Kottirsch, et al. (Bioorg. Med. Chem., Lett. 1993, 3. 1675). In other examples, these were utilized as high potency neurokinin NK-2 Receptor Antagonists in accordance with Deal, et al. (J. Med. Chem. 1992, 35, 4195).

Most of the procedures utilized hereto for the preparation of substituted of 3-amino-2-oxo-pyrrolidines consisted therein that the appropriate open chain methionine compounds were then converted to their dimethylsulfonium salts and these cyclized with strong bases in appropriate solvents. Friedinger, et al, (J.Org. Chem. 1982, 47, 104–109) utilized methyl iodide and sodium hydride for this purpose which reagents are difficult to handle in industrial scale processes. U.S. Pat. No. 5,484,946 substitutes trimethyl sulfonium, in particular trimethyl sulfoxonium salts for the volatile methyliodide. The cyclization can then be carried out with potassium carbonate.

A substantial disadvantage of this procedure is the inevitable release of the intensively malodorous dimethyl sulfide in the methionine prior step. A further disadvantage appears to be the required utilization of expensive aprotic polar solvents such as dimethylsulfoxide in the cyclization with potassium carbonate. In WO 94/2282, there is mentioned a procedure wherein racemic homoserine derivatives which are derived from butyrolactone, are cyclized to pyrrolidones utilizing trimethylphosphene and azocarbonic acid esters. Again, these reagents are not suitable in an industrial scale process, since they are relatively expensive. Furthermore, this procedure gives rise to a number of byproducts during the cyclization whose separation from the desired product is difficult and therefore time and expense-intensive (K. Nakajima, et al., Peptide Chemistry 1983, 77–80).

The conversion of methionine, in particular N-acylmethionines with halocarboxylic acids are known (G. Toennies, J.L. Colb, J.Am.Chem.Soc. 67, 849 (1945); H.G. Gundlach, S. Moore, W.H. Stein, J.Biol.Chem. 234, 1761 (1959), in which the corresponding carboxymethylsulfonium salts are described as unstable compounds which according to reaction conditions, convert either under substitution to homoserine or homoserine lactone derivatives, or under elimination either back to the starting product. This relative unstability was utilized for the conversion of methionine with bromoacetic acid to homoserine lactone (S. Natelson, E.A. Natelson, Microchemical Journal, 40, 226–232 (1989)).

As the only reaction of a N-acyl-methionine-amide with a haloacetic acid, there is reported the conversion of β-endorphin in milligram quantities with a 25% excess via iodoacetic acid to the corresponding s-carboxymethylmethionine analogue (L.Graf, et al., Neuropeptides, 1, 47, 1980).

SUMMARY OF THE INVENTION

The present invention is directed to procedures for the preparation of compounds of Formula I and its salts as summarized in the following flow diagram

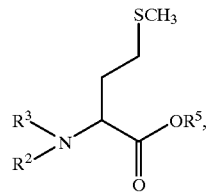
(V)

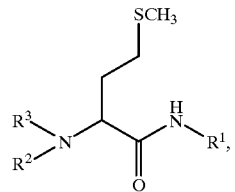
(III)

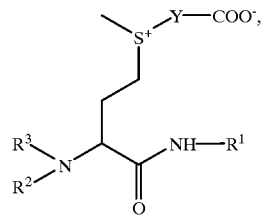
(II)

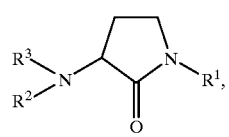
(I)

wherein $R^1$ has the value H, $(C_1-C_8)$-alkyl, $(C_2-C_8)$-alkenyl, $(C_2-C_8)$-alkynyl, $(C_2-C_8)$-alkoxyalkyl, $(C_1-C_8)$-acyl, which can be linear or branched and may be mono or polysubstituted with halogens, and N—, O—, P—, and S— containing residues, $(C_3-C_7)$-cycloalkyl, which may be saturated and unsaturated, as well as substituted with linear or branched chain $(C_1-C_8)$-alkyl, $(C_2-C_8)$-alkenyl, $(C_2-C_8)$-alkyl, $(C_1-C_8)$-acyl, $(C_1-C_8)$-alkoxy, $(C_2-C_8)$-alkoxyalkyl, which may be substituted with halogen, or N—, O—, P—, S-atom containing residues. Said cycloalkyls may contain ring-heterosubstitutions selected from the group consisting of N, O, P, and S, aryl, such as phenyl or naphthyl, aralkyl such as benzyl or phenoethyl, heteroaryl such as furyl, pyrrolyl, pyridyl, heteroaralkyl, such as furfuryl, pyrrolylmethyl, pyridylmethyl, furylethyl, pyrrolylethyl, pyridylethyl, whereby the above rings may be mono or substituted with linear or branch chain $(C_1-C_8)$-alkyl, $(C_2-C_8)$-alkenyl, $(C_2-C_8)$-alkynyl, $(C_1-C_8)$-acyl, $(C_1-C_8)$-Alkoxy, $(C_2-C_8)$-Alkoxyalkyl, with halides with nitriles, with $C(O)NH_2$ or N—, O—, P—, or S-containing residues or N-connected amino acids or peptide residues, $R^2$ has the values of $R^1$ other than N-connected amino acids or peptide residues, $R_3$ may be hydrogen, $(C_1-C_8)$-acyl which may linear or branched, a C-connected amino acid or peptide residue or an appropriate peptide protecting group such as formyl, carbamoyl, benzyloxycarbonyl, tert.-butyloxycarbonyl, allyloxycarbonyl, or trifluoracetyl.

Y is a linear or branched ($C_1$–$C_8$)-alkyl residue which if desired, may be multiply substituted with ($C_1$–$C_4$)-alkyl, halogen, hydroxy or phenyl, ($C_7$–$C_{15}$)-arylalkyl, which may similarly be substituted with ($C_1$–$C_4$)-alkyl, halo or hydroxy, Furthermore, the invention is directed to new intermediates of Formula II

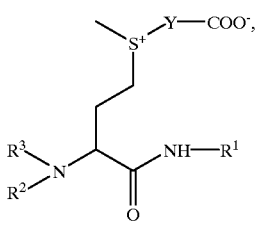
(II)

as well as the acid addition salts thereof, wherein $R^1$, $R^2$, $R^3$ and Y have the above-identified values and a procedure for their production as well as their use.

The compounds producible by the procedures of the present invention and the new intermediates are valuable intermediates for the production of bioactive materials.

The task of the present invention therefore is the provision of a further procedure for the preparation of gamma-lactams of Formula I which avoid the disadvantages of the state of the art and may be advantageously carried out on a technical scale, that means that the utilization of critical substances as well as expensive reagents should be avoided. Under the term critical substances as used in the context of the present invention, there are understood compounds which when utilized on the industrial scale, carry substantial risks either with respect to the environment or danger to workers. It is a further task of the present invention to provide advantageous precursors for the synthesis of gamma-lactams of general Formula I, processes for their production and advantageous application of these precursors.

The solution of these and other so-far undescribed tasks which may be deduced from the state of the art are the efficient conversion of a compound of formula III either directly into a compound of formula I or indirectly via a compound of formula II. A procedure is also described for the provision of compounds of formula II. The use of these latter compounds as pharmaceutical intermediates is also described.

DISCUSSION OF THE PREFERRED EMBODIMENTS

The simple process of the reaction, the good yields, and the avoidance of dangerous or ill-smelling reagents destine this procedure for industrial scale use. The above-described cyclization can proceed under basic conditions wherein as bases, there are utilized tertiary amines such for example, triethylamine, tributylamine or inorganic bases such as alkali or alkaline earth oxides, hydroxides or carbonates. Particularly suitable are such agents such as NaOH, KOH, Ca(OH)$_2$, Na$_2$CO$_3$, K$_2$CO$_3$, Ca$_2$CO$_3$, CaO, NaHCO$_3$, or KHCO$_3$. It is particularly desirable to utilize a solid alkali carbonate and particularly preferred is the use of potassium carbonate for the cyclization.

The cyclization is preferably carried out in polar protic solvents. Particularly preferred for this purpose is methanol.

It is particularly desirable to carry out the procedure with compounds of Formula II wherein Y is CH$_2$. Furthermore, it is highly desirable where the compounds wherein in the compounds of Formula II are $R^1$ is p-cyanophenyl or p-carbamoylphenyl, while $R^2$ is advantageously hydrogen and $R^3$ is benzoyl-oxycarbonyl.

The cyclization may take place in a temperature range of 0° C. to 150° C., between 20° C. to 100° C., most preferably between 40° C. and 70° C.

The synthesis of the compounds of Formula I can proceed preferably and exceedingly simply from procedures in which compounds of Formula II are formed in situ from compounds of Formula III and further reacted without the need for isolation of compounds of Formula II.

In order to obtain derivatives of compounds of type I, it may be necessary to carry out further reactions. These reactions concern reactions for the removal of protecting groups from which compounds of Formula I may be obtained and which are readily known to those skilled in the art. An example of such a conversion may be found in Example 4 hereof.

The compounds of Formula III can be prepared in accordance with ways known in the art (Houben-Weyl, Band 15, Teil 2) from compounds of Formula V

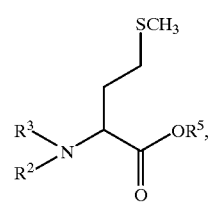
(V)

in which $R^2$, $R^3$, have the above-identified meanings and $R^5$ is hydrogen which can be formed by reaction with means of formula H$_2$N R$^1$ (R$^1$ has the meaning given above).

The compounds of Formula I are readily prepared from compounds of Formula III

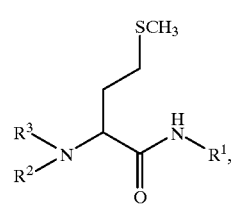
(III)

wherein $R^1$, $R^2$, $R^3$ have the above-identified meanings by reaction with a halocarboxylic acid of Formula IV

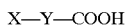

X—Y—COOH (IV), wherein Y has the above-identified meaning and X is halogen, suitably in the presence of a base. Suitable for the conversion of compounds of Formula I, are the following particular compounds of Formula IV:

α-chloroacetic acid, (α-bromoacetic acid, 3-chloro-, bromo- or iodopropionic acid, 4-chloro- or bromobuteric acid, 2-bromoisobuteric acid, 3-chloropivalic acid, α-bromophenylacetic acid, 2-bromoisovaleric acid, 2-bromopropionic acid, 2-bromobuteric acid, 2-bromovaleric acid, 2-bromhexanoic acid, 2-chloropropionic acid, 2-bromoctanoic acid, 5-chloro- or bromovaleric acid, 6-bromo-hexanoic acid, 3-chloro-n-buteric acid, 2-bromo-3-methylvaleric acid, 2-chloro-n-buteric acid, α-chlorophenyl acetic acid, 2-chloro-3-phenyl-propionic acid, 2-chloropentanoic acid, 2-chloro-3-methylbuteric acid, 4-bromomethyl-benzoic acid, 4-chloromethylbenzoic acid, 4-bromomethyl-phenyl acetic acid, 4-(2-chloro-ethyl) benzoic acid, p-(β-bromomethyl)benzoic acid, 4-(α-bromomethyl) benzoic acid, 3-bromomethylbenzoic acid, 3-bromo-buteric acid, bromopivalic acid, 3-chloro lactic acid.

It is preferred to use α-halo carboxylic acid and in particular α-halo acetic acids. As a halogen, it is preferred to use chloro or bromo, as bases there may be utilized tertiary amines such as triethylamine, tributylamine or inorganic bases such as alkali or alkali earth metal oxides, hydroxides or carbonates or alkali alcoholates such as for example sodium methylate or sodium ethylate. In particular as bases, there may be utilized NaOH, KOH, $Ca(OH)_2$, $Na_2CO_3$, $K_2CO_3$, $CaCO_3$, CaO, $NaHCO_3$, or $KHCO_3$. It is preferred to utilize a solid alkali hydroxides and it is particularly preferred to utilize potassium hydroxide. In addition to α-halo carboxylic acids, β-halo carboxylic acids may also be utilized.

In principle, all solvents may be utilized in which the products have a sufficient solubility. Preferred however are polar protic solvents such as water, alcohol, ketones or solvent mixtures containing these. Particularly preferred for the reaction is methanol or acetone. When utilizing solvents with which the halocarboxylic acids could react such as bromoacetic acid and water to glycolic acid, an excess of the halocarboxylic acid is used. In the reaction with bromoacetic acid in methanol and potassium hydroxide as a base a 1.5 excess has generally been found most suitable.

Depending on the halocarboxylic acid used, the reaction may be carried out between −20° C. and 150° C. Where bromoacetic acid is used a temperature of 20–100° C. and particularly 40–80° C. is utilized.

Needless to say, that in place of halocarboxylic acids derivatives of course can be used, in particular the esters of the acids. The reaction follows in a similar manner to that described above. Before the commencement of the cyclization of course, the esterification to the appropriate acid must occur which can be carried out in ways well known to the art. Particularly preferred are halocarboxylic acid derivatives of the Formula I wherein the hydrogen atom is replaced by $(C_1-C_4)$-alkyl, $(C_2-C_6)$-alkenyl, $(C_2-C_6)$-alkoxyalkyl; and phenyl which may be substituted by $(C_1-C_3)$-alkyl or halo, benzyl or phenethyl.

A further aspect of the present invention is directed to advantageous and new intermediates of Formula II,

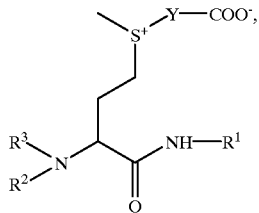

(II)

as well as their acid addition salts in which $R^1$, $R^2$, $R^3$ and Y have the above-identified meaning. Particularly preferred thereby are compounds wherein $R^2$ is hydrogen, $R^3$ is a benzoyloxycarbonyl residue and Y is —$CH_2$—. Particularly preferred are compounds wherein $R_1$ is p-cyanophenyl or p-carbonylphenyl.

The compounds of Formula I are, in accordance with the present invention, utilized for the formation of intermediates by bioactive agents. The formation of the compounds of Formula II proceeds as described from derivatives of Formula III with halocarboxylic acids of Formula IV.

It was therefore most surprising to find that methionine derivatives of Formula III may be readily and in good yield converted with halocarboxylic acid into stable compounds of Formula II. The reaction runs in an advantageous manner when, relative to the halocarboxylic acid, there is utilized 1 equivalent of base. As halocarboxylic acid, it is particularly preferred to use haloacetic acids and in particular bromo-chloroacetic acid. In the case of chloroacetic acid, there may be added for acceleration of the reaction, between 1 and 20 mol % of an alkali iodide, in particular potassium iodide. As bases alkali alkoxides and alkali hydroxides are preferred.

The cyclization of II to I proceeds via an intramolecular nucleophilic substitution and runs substantially analogously to that of the corresponding sulfonium salts (U.S. Pat. No. 5,484,946). In general, all variants known to one skilled in the art may be utilized in this reaction. However, because of the instability of the carboxymethyl sulfonium salt, a series of byproducts will occur. For example, elimination or substitution of the leaving group or decarboxylation to the corresponding dimethylsulfonium salt must be reckoned with. It was therefore most surprising that conditions could be found for the cyclization which permit the use of relatively strong bases, i.e., tertiary amines, alkali or alkali earth metal alkoxides, hydroxides, or carbonates, in the presence of polar protic solvents and nevertheless, allow the broadest selectivity of reaction. These very economical and uncritically useable reagents in industrial state process are preferred from the state of the art for intramolecular substitutions, (no sodium hydride utilization, no expensive reagents or solvents). The methylmercaptocarboxylic acids released in the cyclization have a very low vapor pressure. In particular, when they are in the salt form and thus lead, in contrast to the liberation of dimethyl sulfide from dimethyl sulfonium salts to no substantially offensive odors.

A further advantage of these preferred reaction conditions is that the optical activity of an enantiomer-enriched starting materials under the conditions of the present invention are substantially completely maintained. As the comparison experiment to the embodiments set forth in U.S. Pat. No. 5,484,946 shows, there is in fact a lower amount of racemization (see examples).

It is referred to utilize derivatives of II in the reaction, wherein the residue $R^1$ is p-cyanophenyl or p-carbamoylphenyl. $R^2$ is hydrogen and $R^3$ is benzyloxycarbonyl. These lead to advantageous compounds which can be used for the production of pharmaceuticals as is described, for example, in WO 94/22820.

As solvents for the conversion of II into I, all organic solvents may be utilized which, under the condition of the reaction are inert. Particularly preferred are alcohols, for example methanol, ethanol and ether such as methyl-tert.-butyl ether, tetrahydrofuran, dimethoxyethane, dioxane, hydro-carbons such as for example hexane, cyclohexane, toluene, ketones, for example acetone, dimethyl ketone, methylisobutyl ketone, nitriles, for example acetonitriles and carboxylic acid alkyl esters, for example ethyl acetate, isopropyl acetate, and n-butyl acetate. Particularly preferred are those solvents for example, the mixtures in which the sulfonium salts of Formula I are formed.

As linear or branch chain $(C_1-C_8)$-alkyl residues there may be considered methyl, ethyl, n-propyl, isopropyl, n-butyl, isobutyl, sec-butyl, tert.-butyl, pentyl, hexyl, heptyl or octyl, together with all of their structural isomers. The linear or branch chained $(C_2-C_8)$-alkenyl residues include all substituents which have been discussed with respect to the $(C_1-C_8)$-alkyl residues with exception of the methyl residue, wherein in these moieties there must be at least one double bond. The scope of $(C_2-C_8)$-alkynyl is similar to that of $(C_2-C_8)$-alkenyl. However there must be at least one triple bond. The term $(C_1-C_8)$-alkoxy corresponds to the term $(C_1-C_8)$-alkyl with the condition that this connected to the ring via an oxygen atom. Under the term $(C_2-C_8)$-alkoxyalkyl meant an alkyl chain interrupted by at least one oxygen function whereby two oxygen functions are not connected to each other. The number of carbon atoms gives the total number of carbon atoms in the moiety as $(C_2-C_8)$-alkenyloxy, one understands a $(C_2-C_8)$-alkoxy residue having at least one C—C-double bond. N—, O—, P—, S-atom containing moieties are, in particular alkyl, alkenyl, and alkynyl moieties of the above-described type in which one or more of these hetero atoms is present in the chain or in particular those which bound to the molecule via this hetero atom. By the term $(C_3-C_7)$-cycloalkyl there is understood cyclopropyl, cyclobutyl, cyclo-pentyl, cyclohexyl and cycloheptyl moieties.

In the term halogen, there is included fluorine, chlorine, bromine and iodine.

Under N-connected amino acids or peptide residues, there are intended compounds in which the molecule in question is connected via its N-atom to the α-carbon atom of a carbonic acid residue of an amino acid which can be a portion of the peptide residue.

Under C-connected amino acids or peptide residues, there are intended compounds in which the molecule in question is connected via its N-atom to the carbon atom of a carbonic acid residue of an amino acid which can be a portion of the peptide residue.

Under the term $(C_1-C_8)$-acyl there are included alkyl residues of 1–8 carbon atoms which may be linear or branched including all possible structural isomers thereof which are bound to the molecule via a —C=O.

Under the term $(C_7-C_{15})$-arylalkyl, there is understood an alkyl residue having an aryl residue, suitably phenyl bound thereto. The phenyl can be at the beginning or at the end of the alkyl residue or it may interrupt it. Compounds having stereogenic center between, within the scope of the present invention racemates as well as the enantiomeric antipodes of the structure. However, for the purposes of the present invention, it is preferable to utilize an enantiomer enriched methionine derivatives of Formula III so that during the use of enantiomer enriched starting materials D or L, there is obtained substantially complete stero conservation of the enantioenriched product of the Formula V and I (D or L).

Under the term acid addition salts there are included ionic addition compounds of strong acids such as HCl, HBr, $H_2SO_4$, $H_3PO_4$, $CF_3COOH$, p-toluene sulfonic acid, methansulfonic acid and the molecule in question.

EXAMPLES

Example 1

Preparation of N-Benzyloxocarbonyl-S-carboxymethyl-L-Methionine-4-Cyano-phenylanalide a) Bromoacetic acid 402.4 g (1.04 mole) N-benzyloxocarbonyl-L-methionine-4-cyanophenyl anilide were suspended in 600 ml of methanol and warmed under reflux. At the same time, 217.4 g (1.56 mol) of bromoacetic dissolved in 600 mol water as well as 86 mol (1.64 mol) 50% of sodium hydroxide solution were added dropwise. The now clear reaction mixture was heated under reflux for one hour and subsequently cooled. After a few days a white precipitate was given which was separated, was washed three times with 100 ml of water and after drying yielded 269 g (47%) of a white solid.

(1H-NMR (DMSO). 2.1 (m, 1H), 2.4 (m, 1H), 3.1 (m, 3H), 3.5 (m, 2H), 4.3 (m, 2H), 4.4 (m, 2H), 5.1 (m, 2H), 7.3 (m, 5H), 7,8 (m, 2H), 7.9 (m, 2H), 11.3 (m, 1H).

M.P.: 124–129° C. (decomp.)

b) With chloroacetic acid/potassium iodide 14.0 g (35.8 mmol) N-benzyloxocarbonyl-L-methionine-4-cyano-phenyl anilide 0.15 g (0.9 mmol) potassium iodide was suspended in 14 ml acetone at 70° C. and over 30 minutes reacted with an aqueous solution of 4.1 g (43 mmol) of chloroacetic acid. After a further 30 minutes, HPLC showed only 4.6 Fl. % of N-benzyloxocarbonyl-S-carboxymethyl-L-methioine-4-cyano-phenyl-anilide together with 94.8 Fl. % of the educt. After adjustment of the pH to 5.0 by the addition of 50% sodium hydroxide, after one hour there are already 21 Fl. % and up to 2 hours, 35 Fl. % of product.

Example 2

Formation of (S)-3-Benzyloxocarbonylamino-1-(4-cyanophenyl)-2-pyrrolidinone in Acetonitrile with aqueous sodium hydroxide 25.0 g (46 mmol) N-benzyloxocarbonyl-S-carboxymethyl-L-methio-nine-4-cyanophenylanilidine were suspended in 45 ml of acetonitrile at room temperature. During 5 minutes, 2.3 ml (44 mmol) of 50% aqueous sodium hydroxide were added dropwise and the reaction mixture stirred for 3 hours. Thereafter, a further 0.69 ml (13.2 mmol) of 50% sodium hydroxide were added and the mixture stirred for a further 3 hours. As work-up, 45 ml of water were added and the pH adjusted to 6. The precipitate is separated and yields, after drying, 13.1 g (90%) of a white solid.

M.P.: 192–196° C.

1H-NMR (DMSO): 2.02 (m, 1H), 2.41 (m, 1H), 3.78 (m, 1H), 3.84 (m, 1H), 4.47 (m, 1H), 5.07 (s, 2H), 7.33, 7.38 (m, 5H), 7.77 (d, 1H), 7.88 (dd, 4H).

D-Proportion (HPLC): 7.2%

Example 3

Formation of (S)-3-Benzyloxocarbonylamino-1-(4-cyanophenyl)-2-pyrrolidinones without isolation of the N-Benzyloxocarbonyl-S-carboxymethyl-L-methiine-4-cyanophenylanilidines a) With bromoacetic acid in methanol and aqueous sodium hydroxide/potassium carbonate 38.6 g (100 mmol) N-benzyloxocarbonyl-L-methionine-4-cyanophenyl-anilide was suspended in 60 ml of methanol and warmed to 60° C. Thereafter, 20.8 g (150 mmol) bromoacetic acid dissolved in 50 ml of methanol, as well as 6 ml (114 mmol) of 50% sodium hydroxide were dropped in over 1.75 hours. The clear reaction mixture was stirred for a further 2 hours at 60° C. After cooling to room temperature (RT) the precipitate was separated and treated with 6.9 g (50 mmol) sodium carbonate and warmed to 60° C. After cooling to room temperature (RT) 75 ml of water were added and adjusted to pH 1.5 by the addition of concentrated hydrochloric acid. The precipitate was filtered off and washed twice with 10 ml of water to yield on drying 12.5 g (75%) of a white solid.

D-Proportion (HPLC): 11.5% b) With bromoacetic acid in methanol and methylisobutylketone/acetonitrile and aqueous sodium hydroxide 11.0 g (28.5 mmol) N-benzyloxocarbonyl-L-methionine-4-cyanophenyl-anilide was suspended in 15 ml of methanol and warmed to 60° C. Thereafter, 6.06 g (42.75 mmol)

bromoacetic acid dissolved in 15 ml methanol as well as 2.3 ml (42.75 mmol) 50% aqueous sodium hydroxide were dropped in over 70 minutes. The clear reaction mixture was stirred for a further 2 hours at 60° C. after cooling to room temperature and neutralization, 100 ml of methylisobutyl ketone were added and thereafter distilled off under low vacuum. After cooling to room temperature 15 ml of acetonitrile added and the suspension thereafter treated with 1.3 ml (28 mmol) of 50% aqueous sodium hydroxide and stirred for 1.4 hours at RT. The precipitate was filtered off and washed twice with 10 ml of water to yield 4.5 g (46%) of a white solid.

D-Proportion (HPLC): 4.4% c) With Bromoacetic acid in methanol and potassium hydroxide with potassium carbonate To a suspension of 19.3 g (50 mmol) of N-benzyloxocarbonyl-L-methionine-4-cyanophenylanalide and 10.4 g (75 mmol) bromoacetic acid in 35 ml methanol there was added at 60° C. a solution of 5 g (75 mmol) of 85% potassium hydroxide in 15 ml of methanol. After 4 hours at 60° C. 6.9 g (50 mmol) of potassium carbonate were added and warmed for 3 hours at 60° C. After the addition of 65 ml of water and acidification with concentrated hydrochloric acid to pH 1, the precipitate was filtered off under reduced pressure, washed with water and dried. The yield is 14.5 g (86%) of a white solid.

D-Percentage (HPLC): 12.3% d) With Bromoacetic acid in methanol and potassium hydroxide

The procedure and amounts of the foregoing Example c) were repeated except that the amount of potassium carbonate relative to the N-benzyl-oxocarbonyl-L-methinine-4-cyanophenylanilide were replaced by 1.5 equivalents of 85% potassium hydroxide and the reaction time reduced to 30 minutes. There is obtained 14 g (84%) of a white solid.

D-Proportion (HPLC): 8.4% e) With Bromoacetic acid in methanol with potassium hydroxide as well as sodium methylate 5.0 g (75 mmol) potassium hydroxide were dissolved in 50 ml of methanol and treated with 10.4 g (75 mmol) bromacetic acid. After addition of 19.3 g (50 mmol) N-benzyloxocarbonyl-L-methionine-4-cyanophenylanilide. The mixture was heated for 3 hours at 60° C. and then 63 ml (55 mmol) of 0.87 M sodium methylate solution in methanol were added. After 40 minutes the reaction mixture was brought to pH 1.5 with concentrated hydrochloric acid and cool to 25° C. The precipitate was filtered off, washed with water and dried. There is obtained 9.3 g (56%) of a white solid.

D-Proportion (HPLC): 9.8% f) With Chloroacetic acidipotassium iodide in methanol/methylisobutyl ketone and aqueous sodium hydroxide To 10.0 g (26.1 mmol) N-benzyloxocarbonyl-L-methionine-4-cyano-phenylanilide in 15 ml of methanol, a solution of 2.71 g (28.7 mmol) chloroacetic acid and 1.1 g potassium iodide in 15 ml of water are dropped in over 30 minutes under reflux. After 2 hours, a further 1.3 g of chloroacetic acid are added and the pH adjusted to 5.5 with 50% aqueous potassium hydroxide. After 8 hours the pH is adjusted to 7.1 and reacted with 100 ml of methylisobutyl ketone. Thereafter, the temperature is adjusted to 70° C. under reduced pressure and 13 ml of water azeotropically distilled off. The residue was cooled to room temperature and treated with 1.2 ml (26 mmol) of 50 aqueous sodium hydroxide. After 2 hours the pH was adjusted to 7 and the precipitate filtered off. There was obtained 5.34 g of a 70% pure product.

D-Proportion (HPLC): 3.3%

Example 4

Preparation of 3-Amino-1-(4-cyanophenyl)-2-oxopyrrolidine hydro-chloride (I)

Into a suspension of 50 g (0.15 mol) 3-benzyloxocarbonyl-amino-1-(4-cyanophenyl)-2-oxopyrrolidine in 600 ml of methanol 6.00 g (0.16 mol) of gaseous hydrochloric acid were bubbled in. After addition of 2.5 g 5% palladium on charcoal, hydrogen was bubbled in at 45° C. After 40 minutes, the mixture was cooled, the catalyst filtered off and the filtrate concentrated to dryness. Recrystallization from methanol isopropanol yields 28.50 g (80%) of desired product.

M.P.: 256–258° C. (decomp.)

1H-NMR (DMSO): 2.20 (m, 1H), 2.55 (m, 1H), 3.87 (dt, 1H), 3.97 (t, 1H); 4.27 (dd, 1H), 7.91 (s, 4H), 8.89 (s, 3H).

Example 5

Comparison Experiment: Cyclization of N-Benzyloxocarbonyl-S-methyl-L-methionine-L-methionine-4-cyanophenylanilides sulfonium salts in DMSO 3.12 g (8.2 mmol) N-Benzyloxocarbonyl-L-methionine-4-cyano-phenylanilide were dissolved in 6 ml DMSO and reacted with 5.0 g (24.5 mmol) trimethylsulfonium iodide and 1.69 g (12.2 mmol) of potassium carbonate and heated for 3 hours at 80° C. Thereafter 30 ml of water is added and the precipitate filtered off and washed with water. After drying there is obtained 2.0 g (72%).

D-Proportion (HPLC): 9.2%

What is claimed is:

1. A Process for the preparation of compounds of Formula I and the acid addition salts thereof

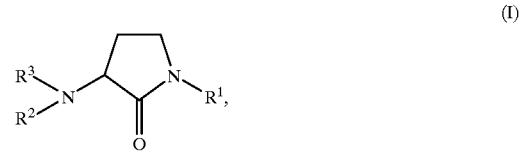

(I)

wherein
R$_1$ is H,
unsubstituted, mono or polysubstituted linear or branched (C$_1$–C$_8$)-alkyl, of(C$_2$–C$_8$)-alkenyl, (C$_2$–C$_8$)-alkynyl, (C$_2$–C$_8$)-alkoxyalkyl, (C$_1$–C$_8$)-acyl, wherein the substituents are selected from the group consisting of halogens, and N—, O—, P—, and S— containing residues, unsubstituted, mono or polysubstituted saturated and unsaturated (C$_3$–C$_7$)-cycloalkyl, wherein the substituents are selected from the group consisting of unsubstituted, mono or polysubstituted linear or branched chain (C$_1$–C$_8$)-alkyl, (C$_2$–C$_8$)-alkenyl, (C$_2$–C$_8$)-alkyl, (C$_1$–C$_8$)-acyl, (C$_1$–C$_8$)-alkoxy, (C$_2$–C$_8$)-alkoxy-alkyl, wherein the substituents are selected from the group consisting of halogen, or N—, O—, P—, S-atom containing residues, unsubstituted, mono or polysubstituted aryl, aralkyl heteroaryl heteroaralkyl, wherein the substituents are selected from the group consisting of linear or branch chain (C$_1$–C$_8$)-alkyl, (C$_2$–C$_8$)-alkenyl, (C$_2$–C$_8$)-alkynyl, (C$_1$–C$_8$)-acyl, (C$_1$–C$_8$)-alkoxy, (C$_2$–C$_8$)-alkoxyalkyl, halo, nitrile, C(O)NH$_2$, N—, O—, P—, or S-containing residues and N-connected amino acids or peptide residues, and ring-heterosubstituents selected from the group consisting of N, O, P, and S, R² has the value as R¹ other than N-connected amino acids or peptide residues, R₃ is hydrogen, linear or branched (C₁–C₈)-acyl a C-connected amino acid or peptide residue or a peptide protecting group by cyclizing a compound of Formula II

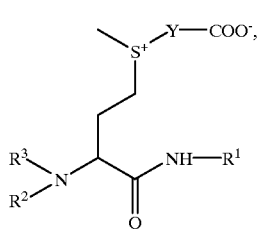

(II)

wherein R¹, R², R³ have the above-identified values and Y is an unsubstituted, mono or polysubstituted linear or branched (C₁–C₈)-alkyl residue wherein the substituents are selected from the group consisting of (C₁–C₄)-alkyl, halogen, hydroxy or phenyl, unsubstituted, mono or polysubstituted (C₇–C₁₅)-arylalkyl, wherein the substituents are selected from the group consisting of (C₁–C₄)-alkyl, halo and hydroxy.

2. Process in accordance with claim 1, wherein the cyclizating agent is a base.

3. Process in accordance with claim 2, wherein the base is selected from the group consisting of potassium hydroxide and potassium carbonate.

4. Process in accordance with claim 1, comprising carrying out the cyclization in a polar protic solvent.

5. Process according to claim 4, wherein the solvent is methanol.

6. Process in accordance with claim 1 wherein Y is —CH₂.

7. Process in accordance with claim 1 wherein in compound II R¹ is cyanophenyl or carbamoylphenyl, R² is hydrogen and R³ is benzyloxy-carbonyl.

8. Process in accordance with claim 1 wherein the cyclization is carried out in a temperature range of between 0 and 150° C.

9. Process for the formation of a compound of Formula II of claim 1 comprising reacting a compound of Formula III

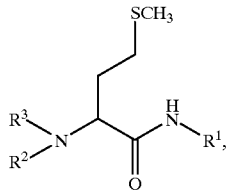

(III)

with a halocarboxylic acid of Formula IV

    (IV)

wherein R¹, R² and R³ and Y are as defined in claim 1 and X is halo.

10. Process in accordance with claim 9 wherein the reaction is carried out in the presence of a base.

11. Process in accordance with claim 10 wherein the base is an alkali hydroxide.

12. Process in accordance with claim 11 wherein the alkali hydroxide is potassium hydroxide.

13. Process in accordance with claim 9 wherein the compound of Formula IV is an α-halocarboxylic acid.

14. Process in accordance to claim 13 wherein the α-halocarboxylic acid is an α-halo acetic acid.

15. Process in accordance with claim 14 wherein the α-halocarboxylic acid is bromacetic acid or chloracetic acid.

16. Process in accordance with claim 9 wherein the reaction is carried out within a temperature range of −20° C. to 150° C.

17. Process in accordance with claim 9 wherein the reaction is carried out in a polar protic solvent .

18. Process according to claim 17 wherein the solvent is methanol.

19. Process for production of a compound of formula I

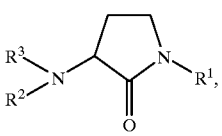

(I)

from a compound of formula III

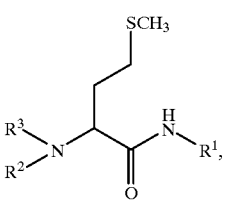

(III)

without the intermediate isolation of a compound of formula II

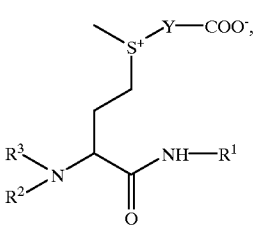

(II)

in the presence of a halocarboxylic acid and a base wherein R¹, R², and R³ Y and X are as defined in claim 9.

20. A compound of Formula II and the addition salts thereof wherein or

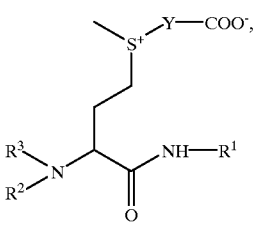

(II)

wherein R¹, R², and R³, and Y are as defined in claim 9.

21. A compound in accordance with claim 20 wherein in Formula I, R² is hydrogen and R³ is benzyloxycarbonyl and Y is —CH₂—.

22. A compound of claim 21 wherein in Formula II, $R^2$ is hydrogen and $R^3$ is benzyloxycarbonyl, Y is $CH_2$ and $R^1$ is cyanophenyl or p-carbamoyl-phenyl.

23. The process of claim 1 wherein aryl is phenyl or naphthyl, aralkyl is benzyl or phenethyl, heteroaryl is furyl, pyrrolyl, pyridyl, heteroaralkyl is furfuryl, pyrrolylmethyl, pyridylmethyl, furylethyl, pyrrolylethyl, pyridyl-ethyl and peptide protecting groups are formyl, carbamoyl, benzyloxy-carbonyl, tert.-butyloxycarbonyl, allyloxycarbonyl, or tri-fluoracetyl.

24. The compound of claim 20 wherein aryl is phenyl or naphthyl, aralkyl is benzyl or phenethyl, heteroaryl is furyl, pyrrolyl, pyridyl, hetero-aralkyl is furfuryl, pyrrolylmethyl, pyridylmethyl, furylethyl, pyrrolylethyl, pyridylethyl and peptide protecting groups are formyl, carbamoyl, benzyloxycarbonyl, tert.-butyloxycarbonyl, allyloxycarbonyl, or trifluor-acetyl.

25. A process for the preparation of intermediates for bioactive materials from compounds of claim 20.

\* \* \* \* \*